(12) United States Patent
Motoyama et al.

(10) Patent No.: US 9,096,904 B2
(45) Date of Patent: Aug. 4, 2015

(54) METHOD FOR DETERMINING LYMPH NODE METASTASIS IN CANCER OR RISK THEREOF AND RAPID DETERMINATION KIT FOR THE SAME

(75) Inventors: Satoru Motoyama, Akita (JP); Masatomo Miura, Akita (JP); Junichi Ogawa, Akita (JP)

(73) Assignee: NATIONAL UNIVERSITY CORPORATION AKITA UNIVERSITY, Akita-shi, Akita (JP)

( * ) Notice: Subject to any disclaimer, the term of this patent is extended or adjusted under 35 U.S.C. 154(b) by 0 days.

(21) Appl. No.: 13/322,537

(22) PCT Filed: May 27, 2010

(86) PCT No.: PCT/JP2010/059049
§ 371 (c)(1),
(2), (4) Date: Nov. 25, 2011

(87) PCT Pub. No.: WO2010/137671
PCT Pub. Date: Dec. 2, 2010

(65) Prior Publication Data
US 2012/0135406 A1 May 31, 2012

(30) Foreign Application Priority Data
May 27, 2009 (JP) .................................. 2009-128323

(51) Int. Cl.
*C12Q 1/68* (2006.01)
*C12P 19/34* (2006.01)
*C07H 21/02* (2006.01)

(52) U.S. Cl.
CPC ........ *C12Q 1/6886* (2013.01); *C12Q 2600/118* (2013.01); *C12Q 2600/156* (2013.01)

(58) Field of Classification Search
CPC ........... C12Q 1/6886; C12Q 2600/156; C12Q 2600/106; C12Q 2600/118
See application file for complete search history.

(56) References Cited

PUBLICATIONS

Eklund C.M. et al. Br J Cancer. (Epub May 12, 2009) Jun. 16, 2009;100(12):1846-51.*
dbSNP Submitted SNP(ss) Details: ss8819703 (Oct. 28, 2003), printed from www.ncbi.nlm.nih.gov/projects, pp. 1-3.*
Pennisi E. Science; Sep. 18, 1998; 281, 5384, pp. 1787-1789.*
Juppner H. Bone vol. 17, No. 2, Supplement, Aug. 1995:39S-42S.*
Hegele R.A. Arterioscler Thromb Vasc Biol. 2002;22:1058-1061.*
Carlson et al. "Polymorphisms within the C-reactive Protein (CRP) Promoter Region are Associated with Plasma CRP Levels" Am. J. Hum. Genet., 2005, vol. 77, No. 1, p. 64-77.
Gockel et al. "Significance of preoperative C-reactive protein as a parameter of the perioperative course and long-term prognosis in squamous cell carcinoma and adenocarcinoma of the oesophagus" World J. Gastroenterol., 2006, vol. 12, No. 23, p. 3746-3750.
International Search Report issued in PCT/JP2010/059049 dated Aug. 17, 2010.
Motoyama et al. "CRP genetic polymorphism is associated with lymph node metastasis in thoracic esophageal squamous cell cancer" Ann. Surg. oncol., 2009.09, vol. 16, p. 2479-2485.
Motoyama et al., "Shokudogan kanja no CRP Idenshi Tagata wa Shokudogan Shinten Inshi to naru", Japanese Journal of Gastroenterological Surgery, vool. 41, No. 7, Jul. 1, 2008, p. 1169 (0-1-134).
Szalai at al. "Single-nucleotide polymorphisms in the C-Reactive protein (CRP) gene promoter that affect transcripton factor binding, alter transcriptional activity, and associate with differences in baseline serum CRP level" J, Mol. Med., 2005, vol. 83, No. 6, p. 440-447.
International Preliminary Report on Patentability, dated Dec. 22, 2011, for Application No. PCT/JP2010/059049.
Eklund et al., "C-reactive protein haplotype is associated with high PSA as a marker of metastatic prostate cancer but not with overall cancer risk", British Journal of Cancer, vol. 100 (2009) pp. 1845-1851.
Siemes et al., "C-Reactive Protein Levels, Variation in the C-Reactive Protein Gene, and Cancer Risk: The Rotterdam Study", Journal of Clinical Oncology, vol. 24, No. 33 (2006) pp. 5216-5222.
Supplemental European Search Report issued in EP Application No. 10 78 0625 on Jan. 14, 2013.
Yan et al., "The Relationship between Gene Polymorphism and CRP Level in a Chinese Han Population", Biochemical Genetics vol. 45, No. 1/2 (2007) pp. 1-9.

* cited by examiner

*Primary Examiner* — Stephen Kapushoc
(74) *Attorney, Agent, or Firm* — Birch, Stewart, Kolasch & Birch, LLP

(57) ABSTRACT

The objective of the present invention is to provide a method and a means of rapidly and reliably detecting lymph node metastasis in cancer or the risk of lymph node metastasis. Specifically, the present invention provides a method and a rapid determination kit for detecting lymph node metastasis in cancer or its risk by identifying a certain genetic polymorphism of the human CRP gene, and it is clinically significant in determining the treatment strategy, because effective prediction/determination can be made regarding lymph node metastasis, which is an important phenomenon in cancer progression.

9 Claims, No Drawings

METHOD FOR DETERMINING LYMPH NODE METASTASIS IN CANCER OR RISK THEREOF AND RAPID DETERMINATION KIT FOR THE SAME

TECHNICAL FIELD

The present invention relates to a method for determining lymph node metastasis in cancer and a rapid determination kit for the same.

BACKGROUND ART

Cancer cells from a primary focus metastasize all over the body through blood vessels and lymphatic vessels. Because the primary focus is removed as much as possible in cancer surgery, the accurate detection of metastasis and the appropriate treatment depending on the degree of metastasis are necessary. Therefore, diagnosing lymph node metastasis by cancer cells is extremely important for selecting the appropriate treatment for cancer.

The diagnosis of lymph node metastasis by cancer cells is broadly divided into pretreatment diagnostic imaging and posttreatment (postoperative) pathological diagnosis. The diagnostic imaging methods that are used for detecting lymph node metastasis in cancer (inspection for the presence of lymph node metastasis) include computed tomography (CT); positron emission tomography (PET); PET-CT, which uses an apparatus integrating PET and CT; and endoscopic ultrasoundscopy (EUS); however, the diagnostic imaging methods have difficulty or only limited availability in detecting microscopic lymph node metastasis. On the other hand, pathological diagnosis method utilizes specimens prepared from a number of excised lymph node tissues under a microscope and is a highly accurate and reliable diagnostic method; however, the diagnosis can only be made using excised lymph nodes as posttreatment (postoperative) diagnosis and therefore cannot be used for selecting the optimum treatment in advance. The diagnosis of lymph node metastasis by cancer cells is problematic in that the pretreatment diagnosis depends on the diagnostic imaging, which is currently less accurate, whereas reliable diagnosis is made in the posttreatment (postoperative) pathological diagnosis.

Therefore, molecular diagnostic techniques using molecular markers are important in the diagnosis of lymph node metastasis by cancer cells, and several techniques have been developed. Many conventionally known molecular diagnostic techniques utilize a protein (target protein) that is not expressed or expressed at a lower level in normal cells and is highly expressed in cancer cells or a nucleic acid (target nucleic acid, as a general term for DNA, mRNA, cDNA, etc.) included in a gene encoding the target protein. Specifically, a target protein included in lymph node tissues resected/excised from a living body is detected using an immunoassay, or conversely, a target nucleic acid is amplified using loop-mediated isothermal amplification (LAMP) or polymerase chain reaction (PCR) to detect the amplification product using a known method to determine the presence of metastatic cancer cells.

Regarding molecular diagnostic techniques, for example, Patent Literature 1 (Japanese Laid-Open Patent Publication No. 2007-175021) proposed a method for determining the presence of lymph node metastasis by colon cancer cells using the mRNA or a fragment of a gene encoding at least one protein selected from the group consisting of PIGR, CLDN3, LGALS4, AGR2, TACSTD1, GPX2, RAI3, TSPAN1, CKB, ELF3, FXYD3, CDH1, REG4, GDF 15, CLDN4, OLFM 4, CD9, CDH17, SELENBP, LCN2, TMPRSS4, CFTR, TM4SF3, ID1, CYP2S1, TFF3, EHF, FAT, KLF5, SLC9A3R2, HOXB9, ATP1B1, PCK1, and FCGBP. Patent Literature 2 (Japanese Laid-Open Patent Publication No. 2007-037421) described the determination of lymph node metastasis in colon cancer by entering the value of expression of a gene set represented by the database access numbers (serial numbers) NM_003404 (G1592), NM_002128 (G2645), NM_052868 (G3031), NM_005034 (G3177), NM_001540 (G3753), NM_005722 (G3826), and NM_015315(G4370) into a mathematical function. Patent Literature 3 (Japanese Laid-Open Patent Publication No. 2008-020438) describes that lymph node metastasis, e.g., from breast cancer, can be determined with higher reliability by determining the expression of a polypeptide related to cytokeratin in a sample prepared from lymph node tissue.

On the other hand, it was recently determined that inflammatory responses promote carcinogenesis by damaging DNA, stimulating angiogenesis and cell proliferation, and inhibiting apoptosis. In this regard, serum C-reactive protein (CRP) has been investigated as a risk factor and a prognostic factor in colon (Non Patent Literature 1: Erlinger T. P. et al., *JAMA* 2004; 291; 585-590), esophageal (Non Patent Literature 2: Shimada H. et al., *J. Surg. Oncol.* 2003; 83; 248-252), hepatocellular (Non Patent Literature 3: Hashimoto K. et al., *Cancer* 2005; 103; 1856-1864), renal (Non Patent Literature 4: Miyata Y. et al., *Urology* 2001; 58; 161-164), and ovarian (Non Patent Literature 5: Hefler L. A. et al., *Clin. Cancer Res.* 2008; 14; 710-714) cancers.

A higher serum CRP level is considered to be associated with a higher risk of developing cancer. For example, Non Patent Literature 6 (Nozoe T. et al., *Am. J. Surg.* 1998; 176 (4):335-8) describes that liver metastasis and lymph node metastasis in colon cancer patients are associated with preoperative increases in serum CRP levels, Non Patent Literature 7 (Nozoe T. et al., *Am. J. Surg.* 2001; 182(2), 197-201) describes that lymph node metastasis in esophageal cancer patients is associated with preoperative increases in serum CRP levels, and Non Patent Literature 8 (Ines G. et al., *World J. Gastroenterol.* 2006; 12(23), 3746-3750) describes that a higher serum CRP level in esophageal cancer patients is associated with lymph node metastasis.

It has been reported that genetic polymorphisms are strongly related to serum CRP levels (Non Patent Literature 9: Carlson C. S. et al., *Am. J. Hum. Gen.* 2005; 77; 64-77 and Non Patent Literature 10: Szalai A. J. et al., *J. Mol. Med.* 2005; 83; 440-447).

Therefore, the present inventors examined whether CRP genetic polymorphisms act as cancer progression factors in esophageal cancer patients. Although we consequently revealed the potential association of CRP-717T>C genetic polymorphisms with lymph node metastasis (Non Patent Literature 11: Motoyama et al., *The Japanese Journal of Gastroenterological Surgery*, vol. 41, No. 7, pp. 1169, July 2008), a technique for detecting lymph node metastasis by cancer cells using the CRP-717T>C genetic polymorphism suffered from lower determination accuracy and was not put into practical use because metastasis was not statistically significant.

CITATION LIST

Patent Literature

[Patent Literature 1] Japanese Laid-Open Patent Publication No. 2007-175021
[Patent Literature 2] Japanese Laid-Open Patent Publication No. 2007-037421
[Patent Literature 3] Japanese Laid-Open Patent Publication No. 2008-020438

Non Patent Literature

[Non Patent Literature 1] Erlinger T. P. et al., *JAMA* 2004; 291; 585-590
[Non Patent Literature 2] Shimada H. et al., *J. Surg. Oncol.* 2003; 83; 248-252
[Non Patent Literature 3] Hashimoto K. et al., *Cancer* 2005; 103; 1856-1864
[Non Patent Literature 4] Miyata Y. et al., *Urology* 2001; 58; 161-164
[Non Patent Literature 5] Hefler L. A. et al., *Clin. Cancer Res.* 2008; 14; 710-714
[Non Patent Literature 6] Nozoe T. et al., *Am. J. Surg.* 1998; 176(4):335-8
[Non Patent Literature 7] Nozoe T. et al., *Am. J. Surg.* 2001; 182(2), 197-201
[Non Patent Literature 8] Ines G. et al., *World J. Gastroenterol.* 2006; 12(23), 3746-3750
[Non Patent Literature 9] Carlson C. S. et al., *Am. J. Hum. Gen.* 2005; 77; 64-77
[Non Patent Literature 10] Szalai A. J. et al., *J. Mol. Med.* 2005; 83; 440-447
[Non Patent Literature 11] Motoyama et al., *The Japanese Journal of Gastroenterological Surgery* vol. 41, No. 7, pp. 1169, July 2008

SUMMARY OF INVENTION

Technical Problem

Regarding methods to detect lymph node metastasis by cancer cells using a conventionally known molecular diagnostic technique, as described in the methods of Patent Literatures 1 to 3, an attempt to reliably detect lymph node metastasis requires a comprehensive investigation of multiple molecular markers as factors for determination and the necessity of using lymph nodes, which greatly torment patients and require considerable time and effort for sample preparation. Serum CRP levels often fluctuate due to the influences of age, smoking, and inflammation. Moreover, the association of the CRP-717T>C genetic polymorphism with lymph node metastasis by cancer cells, as described by Non Patent Literature 11, was later denied. Therefore, a new molecular marker for rapidly and reliably detecting lymph node metastasis by cancer cells and a molecular diagnostic technique using the molecular marker are desired.

Solution to Problem

As described above, a higher serum CRP level is associated with a certain CRP genetic polymorphism. However, the present inventors have found that the usage of the SNP rs1205 (also referred to as CRP1846C>T or rs1205 in this description) as a molecular marker dramatically improves the determination accuracy of lymph node metastasis in cancer and is extremely useful, which is not assumed from the conventional prediction that a CRP genetic polymorphism related to a high serum CRP level may act as a cancer progression factor, thereby completing the present invention. The SNP rs1205 is a one-base mutation in a nontranscribed region of the CRP gene that has been reported to be correlated with a decrease in serum CRP levels.

The present invention provides the following determination method and determination kit:

[1] A method of determining lymph node metastasis in cancer or the risk thereof by identifying a genetic polymorphism in the human C-reactive protein (CRP) gene

[2] The method according to item 1 above, wherein lymph node metastasis in cancer or the risk thereof is determined by identifying a genetic polymorphism SNP rs1205

[3] The method according to item 2 above, wherein the risk is considered to be high when the genotype of SNP rs1205 is T/T

[4] The method according to any one of items 1 to 3 above, wherein the genotype is identified by restriction fragment length polymorphism (RFLP) or by analyzing its binding to a corresponding complementary strand sequence

[5] The method according to item 4 above, wherein the genotype is identified by PCR-RFLP

[6] The method according to item 5 above, wherein a forward primer, 5'-CTT ATA GAC CTG GGC AGT-3' (SEQ ID No. 1), and a reverse primer, 5'-GGA GTG AGA CAT CTT CTT G-3' (SEQ ID No. 2), are used for PCR and Bst4CI is used as a restriction enzyme

[7] The method according to any one of items 1 to 6 above, wherein the cancer is a solid cancer

[8] A rapid determination kit for PCR-RFLP for detecting lymph node metastasis in cancer or the risk thereof, in which the kit comprises primers for amplifying a region containing SNP rs1205 of base sequence of human C-reactive protein gene and a restriction enzyme for detecting the genotype of SNP rs1205 by RFLP

[9] The rapid determination kit according to item 8 above, comprising a forward primer, 5'-CTT ATA GAC CTG GGC AGT-3' (SEQ ID No. 1), and a reverse primer, 5'-GGA GTG AGA CAT CTT CTT G-3' (SEQ ID No. 2), as a primer pair

[10] The rapid determination kit according to item 9 above, comprising the restriction enzyme Bst4CI

[11] A nucleic acid for analyzing bases of the SNP identification number rs1205 of human C-reactive protein gene, the nucleic acid specifically hybridizing to a DNA fragment derived from a region containing the bases of the SNP identification number rs1205 of the human C-reactive protein gene, the region being amplifiable by a PCR method using primers of SEQ ID Nos. 1 and 2.

[12] The method according to any one of items 1 to 7 above, wherein the sample used in identifying the genotype of the human CRP gene is selected from the group consisting of whole blood, leukocytes, the primary focus of cancer, lymphatic vessels, and lymph node tissue.

Advantageous Effects of Invention

Although it is known that the production of CRP is associated with various cytokines (interleukins, tumor necrosis factors, interferons, transforming growth factors), the method of the present invention is independent of the levels of various cytokines and can by itself effectively predict/detect lymph node metastasis by cancer cells. The method of detecting lymph node metastasis in cancer using SNP rs1205 is simple compared to conventional methods and yet remains extremely accurate. Therefore, the usage of SNP rs1205 enables the detection of lymph node metastasis with statistical significance. Because effective prediction/detection can be made on the basis of lymph node metastasis, which is an important phenomenon in cancer progression, the method enables the selection of the most reliable and least invasive therapy from options such as surgery involving lymph node dissection, endoscopic resection without lymph node dissection, chemoradiotherapy, chemotherapy, and radiation therapy, making the present invention clinically significant in determining the treatment strategy.

As the current diagnosis of lymph node metastasis of cancer cell has problems in that the pretreatment diagnosis depends on diagnostic imaging, which is currently less accurate, and that reliable diagnosis is as achieved only as a pathological diagnosis, which is a posttreatment (postoperative) diagnosis, the method of the present invention can solve both problems simultaneously.

Moreover, because this method does not require lymph tissue (lymph nodes or lymphatic vessel) to detect the presence of SNP rs1205 (peripheral blood and other substances/tissues can be used instead), patients suffer less, and work load of laboratory personnel is reduced because of the reduced requirements of sample preparation.

DESCRIPTION OF EMBODIMENTS

A. Method of Detecting Lymph Node Metastasis and the Risk Thereof

The CRP gene used in this invention is a gene corresponding to CRP (C-reactive protein). CRP is a type of acute-phase protein produced predominantly by hepatocytes in response to inflammation, and its serum levels are conventionally used as a marker for various acute and chronic inflammatory diseases. The name is derived from a serum protein (present in the β-globulin fraction) causing a precipitation reaction with the C-polysaccharide of *Diplococcus pneumoniae*, and its expression drastically increases in blood from 0.2 μg/mL by a factor of several hundred to one thousand due to infection, inflammation, and tissue damage. CRP is a homopentamer having a molecular weight of one hundred thirty thousand daltons, and its amino acid sequence is homologous to a portion of serum amyloid P-protein, complement C1.

The entire sequence of the CRP gene has been identified (Woo P, Korenberg J R, Whitehead A S, *J. Biol. Chem.*, 260:13384-13388, 1985) and can be retrieved, for example, as Accession No. NG_013007 in the NCBI web site (http://www.ncbi.nlm.nih.gov/nuccore/NG_013007.1?report=gbwithparts&log$=seqview&from=5000&to=7300) (see Table A for the entire base sequence) (SEQ ID NO: 3).

TABLE A

```
   1 taaggcaaga gatctaggac ttctagcccc tgaactttca gccgaataca tcttttccaa
  61 aggagtgaat tcaggccctt gtatcactgg cagcaggacg tgaccatgga gaagctgttg
 121 tgtttcttgg tcttgaccag cctctctcat gcttttggcc agacaggtaa gggccacccc
 181 aggctatggg agagatttga tctgaggtat gggggtgggg tctaagactg catgaacagt
 241 ctcaaaaaaa aaaaaaaaag actgtatgaa cagaacagtg gagcatcctt catggtgtgt
 301 gtgtgtgtgt gtgtgtgtgt gtgtgtgtgt gtggtgtgta actggagaag gggtcagtct
 361 gtttctcaat cttaaattct atacgtaagt gaggggatag atctgtgtga tctgagaaac
 421 ctctcacatt tgcttgtttt tctggctcac agacatgtcg aggaaggctt ttgtgtttcc
 481 caaagagtcg gatacttcct atgtatccct caaagcaccg ttaacgaagc ctctcaaagc
 541 cttcactgtg tgcctccact tctacacgga actgtcctcg acccgtgggt acagtatttt
 601 ctcgtatgcc accaagagac aagacaatga gattctcata ttttggtcta aggatatagg
 661 atacagtttt acagtgggtg ggtctgaaat attattcgag gttcctgaag tcacagtagc
 721 tccagtacac atttgtacaa gctgggagtc cgcctcaggg atcgtggagt tctgggtaga
 781 tgggaagccc agggtgagga agagtctgaa gaagggatac actgtggggg cagaagcaag
 841 catcatcttg gggcaggagc aggattcctt cggtgggaac tttgaaggaa gccagtccct
 901 ggtgggagac attggaaatg tgaacatgtg ggactttgtg ctgtcaccag atgagattaa
 961 caccatctat cttggcgggc ccttcagtcc taatgtcctg aactggcggg cactgaagta
1021 tgaagtgcaa ggcgaagtgt tcaccaaacc ccagctgtgg ccctgaggcc cagctgtggg
1081 tcctgaaggt acctcccggt tttttacacc gcatgggccc cacgtctctg tctctggtac
1141 ctcccgcttt tttacactgc atggttccca cgtctctgtc tctgggcctt tgttcccta
1201 tatgcattgc aggcctgctc cacctcctc agcgcctgag aatggaggta aagtgtctgg
1261 tctgggagct cgttaactat gctgggaaac ggtccaaaag aatcagaatt tgaggtgttt
1321 tgttttcatt tttatttcaa gttggacaga tcttggagat aatttcttac ctcacataga
1381 tgagaaaact aacacccaga aaggagaaat gatgttataa aaaactcata aggcaagagc
1441 tgagaaggaa gcgctgatct tctatttaat tccccaccca tgaccccag aaagcaggag
1501 ggcattgccc acattcacag ggctcttcag tctcagaatc aggacactgg ccaggtgtct
1561 ggtttgggtc cagagtgctc atcatcatgt catagaactg ctgggcccag gtctcctgaa
```

TABLE A-continued

```
1621  atgggaagcc cagcaatacc acgcagtccc tccactttct caaagcacac tggaaaggcc 1681  attagaattg ccccagcaga gcagatctgc ttttttttcca gagcaaaatg aagcactagg 1741  tataaatatg ttgttactgc caagaactta aatgactggt ttttgtttgc ttgcagtgct 1801  ttcttaattt tatggctctt ctgggaaact cctccccttt tccacacgaa ccttgtgggg 1861  ctgtgaattc tttcttcatc cccgcattcc caatataccc aggccacaag agtggacgtg 1921  aaccacaggg tgtcctgtca gaggagccca tctcccatct ccccagctcc ctatctggag 1981  gatagttgga tagttacgtg ttcctagcag gaccaactac agtcttccca aggattgagt 2041  tatggacttt gggagtgaga catcttcttg ctgctggatt tccaagctga gaggacgtga 2101  acctgggacc accagtagcc atcttgtttg ccacatggag agagact r tg aggacagaag 2161  ccaaactgga agtggaggag ccaagggatt gacaaacaac agagccttga ccacgtggag 2221  tctctgaatc agccttgtct ggaaccagat ctacacctgg actgcccagg tctataagcc 2281  aataaagccc ctgtttactt g
```

In genetics, a genetic polymorphism is normally defined as an alteration (mutation) of certain bases present in one gene at a frequency of 1% or more in the population. A number of genetic polymorphisms have been identified in the CRP gene, and the genetic polymorphism SNP rs1205 can preferably be utilized in the present invention. SNP rs1205 is a polymorphism in the $2148^{th}$ nucleotide (base denoted by r) of the CRP gene sequence described in Table A. In this sequence, r indicates that the base is G (guanine) or A (adenine).

Table B (SEQ ID NO: 4) describes the sequence around SNP rs1205 in a sequence complementary to the CRP gene sequence described in Table A.

SNP rs1205 denotes a polymorphism in the 422nd base (base denoted by Y) of the base sequence described in Table B. In this sequence, Y indicates that the base is C (cytosine) or T (thymine).

In the present invention, lymph node metastasis in cancer or the risk thereof is determined by identifying the genotype of this base (C/C (wild-type), C/T (heterozygous), and T/T (homozygous)).

rs1205 is the identification number of the SNP registered in the SNP database of the National Center for Biotechnology Information (dbSNP, NCBI) in the US, and information about

TABLE B

```
  1  CTTTAGTTTT TGCTCCTCAA ATTGGAATAA TGATAGAATG AGAGTACTAA AACCCCCACA

61  ACTGGCCCTA CATGAATGGC CAGCTATCTC AAAAGAGGGA CTGTGCTTGT CAGAGGGAAT

121  CCCTTCAGGG GACTCTTGGA CAGGTTAAAG TGCCATGGAT ATGTTGTGTA ATGGGAAGTG

181  TAAACTTACA GGGACTTGAT TTCAAAGGTC ATTAGAGAAG TTAGCCACAA CTTCTAAAGC

241  AACTATCAGA AAACAGCTTG GACTCACTCA AGTAAACAGG GGCTTTATTG GCTTATAGAC

301  CTGGGCAGTC CAGGTGTAGA TCTGGTTCCA GACAAGGCTG ATTCAGAGAC TCCACGTGGT

361  CAAGGCTCTG TTGTTTGTCA ATCCCTTGGC TCCTCCACTT CCAGTTTGGC TTCTGTCCTC

421  A Y AGTCTCTC TCCATGTGGC AAACAAGATG GCTACTGGTG GTCCCAGGTT CACGTCCTCT

481  CAGCTTGGAA ATCCAGCAGC AAGAAGATGT CTCACTCCCA AAGTCCATAA CTCAATCCTT

541  GGGAAGACTG TAGTTGGTCC TGCTAGGAAC ACGTAACTAT CCAACTATCC TCCAGATAGG

601  GAGCTGGGGA GATGGGAGAT GGGCTCCTCT GACAGGACAC CCTGTGGTTC ACGTCCACTC

661  TTGTGGCCTG GGTATATTGG GAATGCGGGG ATGAAGAAAG AATTCACAGC CCCACAAGGT

721  TCGTGTGGAA AAGGGGAGGA GTTTCCCAGA AGAGCCATAA AATTAAGAAA GCACTGCAAG

781  CAAACAAAAA CCAGTCATTT AAGTTCTTGG CAGTAACAAC ATATTTATAC CTAGTGCTTC

841  ATTTTGCTCT GGAAAAAAAG CAGATCTGCT CTGCTGGGGC AATTCTAATG GCCTTTCCAG

901  TGTGCTTTGA GAAAGTGGAG G
``` rs1205 is available from the NCBI website (http://www.ncbi.nlm.nih.gov/projects/SNP/).

SNP rs1205 can be identified with various known methods capable of detecting genetic polymorphisms, such as polymerase chain reaction (PCR), PCR-restriction fragment length polymorphism (PCR-RFLP), PCR-single strand conformation polymorphism (PCR-SSCP) (e.g., Orita, M. et al., *Proc. Natl. Acad. Sci., U.S.A.*, 86, 2766-2770 (1989)), PCR-specific sequence oligonucleotide (PCR-SSO), an allele-specific oligonucleotide (ASO) hybridization method (e.g., Saiki, *Nature,* 324, 163-166 (1986)) combining the PCR-SSO method and a dot hybridization method, Taq-Man-PCR (Livak, K J, *Genet Anal.*, 14, 143 (1999), Morris, T. et al., *J. Clin. Microbiol.*, 34, 2933 (1996)), an Invader method (Lyamichev et al., *Nat. Biotechnol.*, 17, 292 (1999)), a MALDI-TOF/MS (matrix) method (Haff L A, Smirnov I P, *Genome Res.*, 7, 378 (1997)) using primer extension, a rolling circle amplification (RCA) method (Lizardi P M et al., Nat Genet 19, 225 (1998)), a method using DNA chip or microarray (e.g., Wang D G et al., Science 280,1077 (1998)), primer extension, a Southern blot hybridization method, and a dot hybridization method (e.g., Southern, E., J. Mol. Biol. 98, 503-517 (1975)), and this identification is not particularly limited. The corresponding sequence portion may be analyzed by direct sequencing. These methods can be used in arbitrary combinations. When the method is implemented, primers and probes can be designed from the base sequences described in Tables A and B as needed.

When the identification method is implemented, if the number of target DNA is small, it is preferable to use PCR-based method, e.g., PCR-RFLP, for the identification in terms of detection sensitivity and accuracy. Any of the identification methods may be applied after the test DNA is amplified in advance by PCR or a PCR-based gene amplification method. Conversely, if the identification is performed for a number of target DNA, it is particularly preferable to use methods incorporating DNA chips or microarrays, the Invader method, TaqMan-PCR, and the MALDI-TOF/MS (matrix) method using primer extension or RCA method.

Among the identification methods described above, the preferred method in the case of a small number of target DNA and the preferred method in the case of identification for a large number of target DNA will be described by using representative methods as examples.

The preferred method in the case of a small number of target DNA is preparing a DNA sample from a patient with a method well known to those skilled in the art, followed by cleaving the prepared DNA sample with a restriction enzyme, separating DNA fragments depending on their size, and then comparing the sizes of the detected DNA fragments with that of a control. Typically, a DNA sample is first prepared from a patient and DNA containing the CRP gene is then amplified. The amplified DNA is cleaved by restriction enzyme. DNA fragments are then separated depending on its size and the size of detected DNA fragment is compared with a control.

Such methods include RFLP and PCR-RFLP. In other words, if mutation exists in the recognition site of a restriction enzyme or if a base insertion or deletion exists in a DNA fragment generated by a restriction enzyme, the size of the fragment generated after restriction enzyme treatment is changed compared to that of the control. The portions including this mutation can be amplified by PCR and treated with respective restriction enzymes to detect the mutation as a difference in the mobility of the bands after electrophoresis. Alternatively, after a DNA sample (genomic (chromosomal) DNA is usable) is prepared from a patient, treated with restriction enzymes, and electrophoresed, the presence of a polymorphism (mutation) can be detected by Southern blotting using a DNA probe that may hybridize with a target nucleic acid. The restriction enzymes used can be selected depending on the respective mutations as needed. In this method, in addition to genomic DNA, RNA prepared from patients can be converted into cDNA using reverse transcriptase and directly cleaved with a restriction enzyme to perform Southern blotting. DNA containing the CRP gene can be amplified by PCR using this cDNA as a template and cleaved with a restriction enzyme to examine differences in mobility.

Primers used in the present invention include all of the primers that can amplify DNA containing the CRP gene. The preferred base length of the primers is 10 or more bases, most preferably 15 or more bases. Each of the primers may be a single oligonucleotide or a mixture of a number of oligonucleotides. Examples of the primers used in PCR are a forward primer, 5'-CTT ATA GAC CTG GGC AGT-3' (SEQ ID No. 1), and a reverse primer, 5'-GGA GTG AGA CAT CTT CTT G-3' (SEQ ID No. 2). The restriction enzyme may be Bst4CI. Materials other than the primers and conditions in PCR, application of the restriction enzyme, electrophoresis, detection, and other conditions may be the same as those of commonly used methods.

The DNA probes that can be used in Southern blotting are not particularly limited, provided that the DNA probe can hybridize with the target nucleic acid. An example of a DNA probe hybridizable to the target nucleic acid is that for SNP rs1205 of the human CRP gene, which specifically hybridizes with a DNA fragment containing rs1205 and which is derived from a region amplifiable by PCR using SEQ ID Nos. 1 and 2.

The CRP gene can be acquired from blood cells, peripheral blood leukocytes, skin cells, mucosal cells, liver, kidney, adrenal gland, brain, and uterine tissues, hair, and other tissues of patients by using known extraction and purification methods. A partial- or full-length sequence of the CRP gene may be utilized in the present invention as long as it contains the target base. In other words, a DNA fragment of any length is usable as long as it contains SNP rs1205.

The preferred method in the case of identification for a large number of target DNA is preparing DNA containing the CRP gene derived from a patient and a substrate fixed to nucleotide probes (synonymous with the DNA probes) hybridizing to the DNA, followed by bringing the DNA into contact with the substrate and subsequently detecting DNA (target nucleic acid) hybridizing to the nucleotide probes fixed to the substrate to detect PCR genetic polymorphisms.

Such a method can be well illustrated by a DNA chip method (microarray method). A DNA sample from a patient containing the CRP gene can be prepared with a method well known to those skilled in the art as described above. In the preferred method of DNA sample preparation, DNA is prepared from genomic (chromosomal) DNA extracted from blood, peripheral blood leukocyte, cells such as skin cell, and mucosal cell, tissues such as liver, kidney, adrenal gland, brain, and uterus, hair of patients as described above. To prepare a DNA sample of this method from genomic (chromosomal) DNA, for example, a primer hybridizing to DNA containing the CRP gene can be used for preparing DNA containing the CRP gene with PCR using the genomic (chromosomal) DNA as a template. The prepared DNA sample can be labeled as needed for detection with a method well known to those skilled in the art.

In the DNA chip method, a plurality of DNA probes is aligned and fixed on a substrate of glass or another material to perform hybridization of a labeled DNA sample, and a method of detecting a label (such as fluorescence) signal on the probe is utilized to distinguish and detect complete matches and one-base mismatches through hybridization to detect genetic polymorphisms such as SNPs.

The preferred methods in the case of identification for a large number of target DNA will hereinafter be summarized.

The TaqMan PCR method utilizes PCR of fluorescently labeled allele-specific oligos and Taq DNA polymerase.

The Invader method is the combination of i) the hybridization to template DNAs of two reporter probes specific to respective alleles of genetic polymorphisms such as SNPs and one invader probe, and ii) the cleavage of DNA by an enzyme exhibiting special endonuclease activity that recognizes and cleaves a specific structure of DNA.

The SniPer method can be employed as a method utilizing primer extension. A basic principle of the SniPer method is a technique called rolling circle amplification (RCA), and circular single-stranded DNA is used as a template for DNA polymerase to continuously synthesize complementary-strand DNA. With this method, genetic polymorphisms such as SNPs can be determined by measuring the presence of a color reaction generated when DNA amplification occurs.

The MALDI-TOF/MS method utilizes a mass spectrometer to detect changes in mass due to one-base substitution for genotyping SNPs. Methods utilizing PCR amplification and multiplex PCR are available.

The sequencing method can be used to amplify a region containing a genetic polymorphism using PCR and a dye terminator to sequence DNA to analyze the frequency of genetic polymorphisms such as SNPs.

The determination method of the present invention is applicable to various stages and is particularly useful in the decision of the treatment strategy. For example, for patients with esophageal cancer with submucosal invasion, detection of lymph node metastasis using conventional methods is difficult. On the other hand, the present invention can detect lymph node metastasis or the risk thereof with high accuracy and can therefore avoid the deterioration of QOL due to unnecessary lymph node dissection and prevent cancer from progressing without necessary lymph node dissection.

No particular limitation exists on the types of cancer for which this method is applicable, and the method is applicable to all the solid cancers. Specifically, the method is applicable to cancers with primary focus in the esophagus, lung, breast, head and neck, stomach, colon, biliary tract, pancreas, uterus, ovary, bladder, kidney, urothelium, and prostate gland.

B. Rapid Determination Kit for Lymph Node Metastasis or the Risk Thereof

The present rapid determination kit for lymph node metastasis and the risk thereof can be prepared with a method well known to those skilled in the art. Various reagents necessary for detecting the CRP genetic polymorphism by using the primers of the present invention can be packaged in advance into the kit. Specifically, the reagents provided as a kit include various oligonucleotides used as the primers or loop primers designed for the present invention, four types of dNTP (dATP, dCTP, dGTP, and dTTP) acting as substrates for nucleic acid synthesis, the template-dependent nucleic acid synthesis enzyme exhibiting strand displacement activity, buffer solution providing preferred conditions for the enzyme reaction, salts (e.g., magnesium salt or manganese salt) as cofactors, protectants stabilizing enzymes and templates, and restriction enzyme as well as reagents necessary for detecting reaction products as needed. DNA probes hybridizable to the target nucleic acid may be included in a kit as a component reagent.

Although terms used in this description have normally used meanings, "lymph node" in the "method of detecting lymph node metastasis in cancer or the risk thereof" may be used as a general term for both "lymph node" and "lymphatic vessel" or a term for "lymphoid tissue"; "detection of lymph node metastasis" includes detecting the presence/possibility of cancer cells existing in a lymph node; and "determination of the risk of lymph node metastasis" includes determining the presence/possibility of metastasis of cancer cells from a primary focus to a lymph node if a certain individual has a cancer.

EXAMPLES

Although the present invention will hereinafter be described in more detail with examples, it is not limited to these examples. The following study including experiments/examinations was performed with the approval from the Ethics Committee of Akita University School of Medicine. All the subjects provided informed consent.

Example 1

This example was performed using 113 patients (all Japanese) with thoracic esophageal squamous cell cancer. Thirty-eight of the patients underwent esophagectomy over 1 year beginning in April 2007 after confirmation (e.g., by pathological diagnosis) of esophageal cancer. The remaining 75 patients were selected at random from among those undergoing esophagectomy between 2000 and 2007 and were observed for subsequent cancer progression. The disease was classified in accordance with the International Union against Cancer Tumor-Node-Metastasis (TNM) classification of malignant tumors, 6th edition.

After collecting peripheral blood from the patients, DNA was extracted using a QIAamp Blood Kit (Qiagen) and stored at −80° C. until analysis. The investigation of the association with lymph node metastasis in cancer was performed for CRP1846C>T(rs1205), the example of the present invention, and for 18 other genetic polymorphisms, i.e., CRP polymorphisms CRP-717C>T(rs2794521), CRP1059G>C (rs1800947), and CRP1444C>T(rs1130864); tumor necrosis factor polymorphisms TNF-α-238G>A, TNF-α-308G>A, TNF-α-1031T>C; and TNF-β250G>A, INF-γ874A>T, TGF-β1 29T>C, IL-1β-31C>T, IL-1β-511C>T, IL-1 receptor antagonist, IL-2-330T>G, IL-4-590C>T, IL-6-634G>C, IL-6 receptor 48892A>C, IL-10-592A>C, and IL-12β-1188A>C.

PCR for amplifying target nucleic acids was performed by thermal denaturation of extracted DNA at 95° C. for 15 min, 35 cycles of reaction at 95° C. for 30 s, 56° C. for 30 s, and 72° C. for 30 s, and heating at 72° C. for 5 min. A forward primer, 5'-CTT ATA GAC CTG GGC AGT-3' (SEQ ID No. 1), and a reverse primer, 5'-GGA GTG AGA CAT CTT CTT G-3' (SEQ ID No. 2), were used as primers for amplifying the CRP1846C>T (rs1205) genetic polymorphism. Bst4CI was added to the PCR amplification product acquired from the operation, and after incubation at 65° C. for 8 h, RFLP was performed by electrophoresis.

CRP polymorphisms (a total of four genetic polymorphisms, i.e., the CRP1846C>T (rs1205) genetic polymorphism and three genetic polymorphisms mentioned above) were also investigated in 139 patients (all Japanese) treated for ailments other than cancer in Akita University Hospital as controls.

The frequencies of the appearance of the polymorphisms are consistent with those expected for Hardy-Weinberg equilibrium. The results were similar to those of the SNP500 database of the National Cancer Institute.

Of the 113 esophageal cancer patients studied, 62 patients (55%) had lymph node metastasis, whereas 51 patients (45%) did not have lymph node metastasis. Although patients with pathologically identified lymph node metastasis had significantly (P<0.05) deeper invasion by the cancer than the patients without lymph node metastasis, no significant correlation existed between the presence of lymph node metastasis and age, sex, preoperative nutritional state, tumor markers, tumor site and size, squamous cell and intramural metastasis (see Table 1 "Clinical characteristics of patients with or without lymph node metastasis").

TABLE 1

Clinical characteristics of patients with or without lymph node metastasis

| | Lymph node metastasis | | |
|---|---|---|---|
| | Negative (N = 51) | Positive (N = 62) | P |
| Age (years) | 65 ± 8 | 63 ± 8 | 0.106 |
| Gender | | | |
| Male | 47 | 52 | |
| Female | 4 | 10 | 0.2538 |
| Hemoglobin (g/dL) | 13.6 ± 1.5 | 13.7 ± 1.5 | 0.7718 |
| Albumin (g/L) | 43 ± 3 | 43 ± 3 | 0.4647 |
| SCC (ng/mL) | 1.1 ± 2.9 | 1.1 ± 1.5 | 0.8970 |
| CEA (ng/mL) | 3.5 ± 2.1 | 4.3 ± 2.8 | 0.1022 |
| Preoperative serum CRP (mg/L) | 4.0 ± 8.3 | 4.7 ± 8.1 | 0.6514 |
| Tumor location | | | |
| Upper third | 2 | 5 | |
| Middle third | 31 | 31 | |
| Lower third | 28 | 26 | 0.4305 |
| Tumor size (mm) | 49 ± 29 | 54 ± 25 | 0.3725 |
| Depth of tumor invasion (pT) | | | |
| T1 | 27 | 14 | |
| T2 | 4 | 11 | |
| T3 | 18 | 31 | |
| T4 | 2 | 6 | 0.0078* |
| Tumor differentiation | | | |
| Well-moderately | 41 | 48 | |
| Poorly | 10 | 14 | 0.8184 |
| Lymphatic invasion | | | |
| Positive | 45 | 62 | |
| Negative | 6 | 0 | 0.0071* |
| Venous invasion | | | |
| Positive | 34 | 55 | |
| Negative | 17 | 7 | |
| Intramural metastasis | | | |
| Positive | 4 | 8 | |
| Negative | 47 | 54 | 0.5422 |
| Number of involved lymph nodes | 0 | 3.9 ± 4.9 | <0.001* |

SCC squamous cell carcinoma antigen, CEA carcinoembryonic antigen, CRP C-reactive protein

TABLE 2

Relationship between CRP genotypes and lymph node metastasis

| | Lymph node metastasis | | |
|---|---|---|---|
| CRP genotypes | Negative (N = 51) | Positive (N = 62) | P |
| CRP −717T/C (rs2794521) genotypes | | | |
| T/T | 35 | 50 | |
| T/C | 15 | 12 | |
| C/C | 1 | 0 | 0.2302 |
| T/T | 35 | 50 | |
| T/C + C/C | 16 | 12 | 0.1891 |
| CRP 1059G/C (rs1800947) genotypes | | | |
| G/G | 48 | 58 | |
| G/C | 3 | 4 | >0.9999 |
| CRP 1444C/T (rs1130864) genotypes | | | |
| C/C | 49 | 56 | |
| C/T | 1 | 6 | |
| T/T | 1 | 0 | 0.1350 |
| C/C | 49 | 56 | |
| C/T + T/T | 2 | 6 | 0.2906 |
| CRP 1846C/T (rs1205) genotypes | | | |
| C/C | 6 | 7 | |
| C/T | 29 | 18 | |
| T/T | 16 | 37 | 0.0068* |
| C/C + C/T | 35 | 25 | |
| T/T | 16 | 37 | 0.0043* |

*Significant difference

As a result of the analysis of the association between various genetic polymorphisms and pathologically identified lymph node metastasis, only the CRP1846C>T (rs1205) genetic polymorphism which is utilized in the present invention was significantly associated with lymph node metastasis (Fisher's exact test, P=0.0043). Regarding the CRP1846C>T (rs1205) genetic polymorphism, lymph node metastasis was found in 25 patients and not found in 35 patients with the C/C or C/T genotype, whereas lymph node metastasis was found in 37 patients and not found in 16 patients with the T/T genotype (see Table 2 "Relationship between CRP genetic polymorphism and lymph node metastasis").

On the other hand, with regard to the CRP1059G>C (rs1800947) genetic polymorphism, lymph node metastasis was found in 58 patients and not found in 48 patients with the G/G genotype, whereas lymph node metastasis was found in 4 patients and not found in 3 patients with the G/C genotype. Regarding the CRP-717T>C (rs2794521) genetic polymorphism discussed in Non Patent Literature 11 (Motoyama et al., *The Japanese Journal of Gastroenterological Surgery* vol. 41, No. 7, pp. 1169, July 2008), lymph node metastasis was found in 12 patients and not found in 16 patients with the T/C and C/C genotypes, and regarding the CRP1444C>T (rs1130864) genetic polymorphism, lymph node metastasis was found in 56 patients and not found in 49 patients with the C/C genotype (see Table 2 "Relationship between CRP genetic polymorphism and lymph node metastasis").

As a result of multivariate logistic analysis using the CRP1846C>T (rs1205) genetic polymorphism and various clinical factors related to lymph node metastasis as covariates, it was revealed that the T/T genotype in a patient at rs1205 is significantly associated with lymph node metastasis (odds ratio ≥3). Conversely, as a result of similar analysis of preoperative serum CRP and SCC levels, tumor size, and age, the odds ratio was approximately 1 in each case. A comparison of the depth of tumor invasion (T2 to 4 versus T1) revealed lymph node metastasis involvement at an odds ratio of 2.571 (see Table 3 "Multivariate logistic regression analysis of lymph node metastasis").

TABLE 3

Multivariate logistic regression analysis of lymph node metastasis

|  | β | Wald $\chi^2$ | P | Odds ratio | 95% CI |
|---|---|---|---|---|---|
| CRP 1846C/T genotypes (T/T versus C/C + C/T) | 1.112 | 5.615 | 0.0178 | 3.040 | 1.212-7.625 |
| Preoperative serum CRP | −0.107 | 0.078 | 0.7799 | 0.898 | 0.423-1.907 |
| Serum SCC | 0.070 | 0.252 | 0.6160 | 1.072 | 0.816-1.409 |
| Tumor location (upper versus middle-lower) | 0.608 | 0.297 | 0.5855 | 1.836 | 0.207-16.312 |
| Tumor size | −0.005 | 0.209 | 0.6472 | 0.995 | 0.975-1.016 |
| Depth of tumor invasion (T2-4 versus T1) | 0.944 | 2.700 | 0.1004 | 2.571 | 0.833-7.929 |
| Tumor differentiation (well-moderately versus poorly) | −0.496 | 0.710 | 0.3995 | 0.609 | 0.192-1.930 |
| Venous invasion (positive versus negative) | 1.131 | 2.680 | 0.1016 | 3.099 | 0.800-12.003 |
| Intramural metastasis (positive versus negative) | 0.219 | 0.085 | 0.7705 | 1.245 | 0.285-5.439 |
| Age | −0.049 | 2.246 | 0.1340 | 0.952 | 0.893-1.015 |
| Gender (male versus female) | −0.821 | 1.278 | 0.2582 | 0.440 | 0.106-1.826 |

Likelihood-ratio $\chi^2$ test, $\chi^2$ = 23.241(df = 11), P = 0.0163

With regard to the rs1205 genetic polymorphism, preoperative serum CRP levels were 0-5 mg/L for 43 of the patients with the C/C and C/T genotypes and 43 of the patients with the T/T genotype whereas the levels were greater than 5 mg/L for 16 of the patients with the C/C and C/T genotypes and 8 of the patients with the T/T genotype. (see Table 4 "Relationship between CRP1846C>T (rs1205) genotypes and preoperative serum CRP level, depth of tumor, and number involved lymph nodes").

TABLE 5

Prediction of lymph node involvement in submucosal esophageal cancer using CRP 1846C > T (rs1205) polymorphism or the usual methods (CT and ultrasonography)

|  | Sensitivity (%) | Specificity (%) | Positive predictive value (%) | Negative predictive value (%) |
|---|---|---|---|---|
| CRP 1846C > T (rs1205) polymorphism | 64 | 79 | 69 | 75 |
| Usual methods | 50 | 79 | 54 | 68 |

TABLE 4

Relationship between CRP 1846C/T (rs1205) genotypes and preoperative serum CRP level, depth of tumor, and number of involved nodes

|  | CRP 1846C/T (rs1205) genotypes | | | | CRP 1846C/T (rs1205) genotypes | | |
|---|---|---|---|---|---|---|---|
|  | C/C (N = 13) | C/T (N = 47) | T/T (N = 53) | P | C/C + C/T (N = 60) | T/T (N = 53) | P |
| Preoperative serum CRP (mg/L)[a] | 5.7 ± 5.8 | 4.6 ± 10.6 | 3.8 ± 6.0 | 0.737 | 4.8 ± 9.7 | 3.8 ± 6.0 | 0.0537 |
| 0-5 mg/L | 6 | 37 | 43 |  | 43 | 43 |  |
| >5 mg/L | 7 | 9 | 8 | 0.0107* | 16 | 8 | 0.1706 |
| Depth of tumor invasion (pT) |  |  |  |  |  |  |  |
| T1 | 2 | 24 | 15 |  | 26 | 15 |  |
| T2-4 | 11 | 23 | 38 | 0.0153[a] | 34 | 38 | 0.1184 |
| Number of involved lymph nodes | 1.4 ± 1.9 | 1.8 ± 3.7 | 2.7 ± 4.9 | 0.4605 | 1.7 ± 3.7 | 2.7 ± 4.9 | 0.2284 |
| 0-2 | 11 | 39 | 35 |  | 50 | 35 |  |
| >3 | 2 | 8 | 18 | 0.1038 | 10 | 18 | 0.0487* |

[a]Preoperative serum CRP level was not measured in one patient in C/T genotype group or in two patients in T/T genotype group The diagnosability was extremely high after limiting the analysis to subjects with submucosal esophageal cancer (33 patients), in which diagnosis of lymph node metastasis is particularly difficult and approaches to therapy is significantly influenced by the presence of pretreatment lymph node metastasis. Although the lymph node metastasis diagnosis using the most advanced diagnostic imaging apparatus (CT and ultrasonography) achieved a sensitivity, specificity, positive predictive value, and negative predictive value of 50%, 79%, 54%, and 68%, respectively, the diagnosis using the CRP1846C>T (rs1205) genetic polymorphism achieved a sensitivity, specificity, positive predictive value, and negative predictive value of 64%, 79%, 69%, and 75%, respectively, which were more favorable (see Table 5 "Prediction of lymph node involvement in submucosal esophageal cancer using CRP1846C>T (rs1205) genetic polymorphism or the usual methods (CT and ultrasonography)").

Example 2

Similarly, as a result of investigating the relationship between the CRP1846C>T (rs1205) genetic polymorphism and pathological lymph node metastasis in 152 lung cancer patients (all Japanese) who underwent surgery, a significant relationship between the two was revealed as observed for esophageal cancer (Fisher's exact test, P=0.0312).

As indicated by the results above, according to the present invention, lymph node metastasis or the risk thereof can be detected with high accuracy. In particular, lymph node metastasis or the risk thereof can notably be determined with higher accuracy using the CRP1846C>T (rs1205) genetic polymorphism than with polymorphisms of other cytokines involved in CRP production.

Example 3

The relationship between the CRP1846C>T (rs1205) genetic polymorphism and lymph node metastasis was analyzed in 64 patients having a wall invasion depth of pT1-2 among the 113 subjects of Example 1. Regarding the CRP1846C>T (rs1205) genetic polymorphism, lymph node metastasis was found in 6 patients and not found in 35 patients with the C/C or C/T, whereas lymph node metastasis was found in 18 patients and not found in 5 patients with the T/T genotype. The CRP1846C>T (rs1205) genetic polymorphism was significantly related to lymph node metastasis (Fisher's exact test, P=0.0001). As lymph node metastasis can certainly be detected in early cancer, in which lymph node metastasis may be overlooked by conventional diagnostic imaging methods, it was confirmed that the method of the present invention can meet clinical needs.

Example 4

The relationship between the CRP1846C>T (rs1205) genetic polymorphisms and lymphatic vessel invasion was analyzed in 144 patients implicated for lymphatic vessel invasion among the 152 subjects of Example 2. Regarding the CRP1846C>T (rs1205) genetic polymorphism, lymphatic vessel invasion was found in 36 patients and not found in 42 patients with the C/C or C/T genotype, whereas lymphatic vessel invasion was found in 45 patients and not found in 21 patients with the T/T genotype. The CRP1846C>T (rs1205) genetic polymorphism was significantly related to lymphatic vessel invasion (Fisher's exact test, P=0.008). "Lymphatic vessel invasion" indicates the state in which the presence of cancer cells is observed in lymphatic vessel of the primary focus and suggests the possibility of future "lymph node metastasis" even if no "lymph node metastasis" actually exists. Therefore, identifying the genotype of the CRP1846C>T (rs1205) genetic polymorphism is useful in the determination (prediction in earlier stage) of the risk of "lymph node metastasis."

---

The invention claimed is:

1. A method of treating cancer in a human subject, comprising:
   obtaining a biological sample from the subject, said sample comprising nucleic acids from the subject;
   detecting a T/T genotype of SNP rs1205 in human C-reactive protein (CRP) gene in the nucleic acids;
   correlating the presence of said T/T genotype of SNP rs1205 with an increased risk of lymph node metastasis in the subject; and
   administering to the subject a cancer treatment involving lymph node dissection.

2. The method according to claim 1, wherein the genotype is identified by RFLP or its binding with a corresponding complementary strand sequence.

3. The method according to claim 2, wherein the genotype is identified by PCR-RFLP.

4. The method according to claim 3, wherein a forward primer, 5'-CTT ATA GAC CTG GGC (SEQ ID No. 1), and a reverse primer, 5'-GGA GTG AGA CAT CTT CTT G-3' (SEQ ID No. 2), are used as primers in PCR and Bst4CI is used as a restriction enzyme.

5. The method according to claim 1, wherein the cancer is a solid cancer.

6. The method according to claim 1, wherein the sample is selected from the group consisting of whole blood, leukocytes, the primary focus of cancer, lymphatic vessel, and lymph node tissue.

7. The method according to claim 1, comprising causing a nucleic acid to specifically hybridize with a DNA fragment derived from a region containing SNP rs1205 of the human C-reactive protein (CRP) gene, with the region being amplifiable by a PCR method using primers of SEQ ID Nos. 1 and 2.

8. The method according to claim 5, wherein the solid cancer is selected from the group consisting of: esophagus, lung, breast, head and neck, stomach, colon, biliary tract, pancreas, uterus, ovary, bladder, kidney, urothelium and prostate cancer.

9. The method according to claim 1, wherein the cancer treatment involving lymph node dissection is surgery invoking lymph node dissection.

* * * * *

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Synthetic Forward primer

<400> SEQUENCE: 1
cttatagacc tgggcagt                                                   18

<210> SEQ ID NO 2
<211> LENGTH: 19
<212> TYPE: DNA
<213> ORGANISM: Artificial Sequence
<220> FEATURE:
<223> OTHER INFORMATION: Synthetic Reverse primer

<400> SEQUENCE: 2
ggagtgagac atcttcttg                                                  19

<210> SEQ ID NO 3
<211> LENGTH: 2301
<212> TYPE: DNA
<213> ORGANISM: Homo sapiens
<220> FEATURE:
<221> NAME/KEY: variation
<222> LOCATION: (2148)..(2148)
<223> OTHER INFORMATION: Synthetic G or A

<400> SEQUENCE: 3
taaggcaaga gatctaggac ttctagcccc tgaactttca gccgaataca tcttttccaa     60
aggagtgaat tcaggccctt gtatcactgg cagcaggacg tgaccatgga gaagctgttg    120
tgtttcttgg tcttgaccag cctctctcat gcttttggcc agacaggtaa gggccacccc    180
aggctatggg agagatttga tctgaggtat gggggtgggg tctaagactg catgaacagt    240
ctcaaaaaaa aaaaaaaaag actgtatgaa cagaacagtg gagcatcctt catggtgtgt    300
gtgtgtgtgt gtgtgtgtgt gtgtgtgtgt gtggtgtgta actggagaag gggtcagtct    360
gtttctcaat cttaaattct atacgtaagt gaggggatga atctgtgtga tctgagaaac    420
ctctcacatt tgcttgtttt tctggctcac agacatgtcg aggaaggctt ttgtgtttcc    480
```

| | |
|---|---|
| caaagagtcg gatacttcct atgtatccct caaagcaccg ttaacgaagc ctctcaaagc | 540 |
| cttcactgtg tgcctccact tctcacacgga actgtcctcg acccgtgggt acagtatttt | 600 |
| ctcgtatgcc accaagagac aagacaatga gattctcata ttttggtcta aggatatagg | 660 |
| atacagtttt acagtgggtg ggtctgaaat attattcgag gttcctgaag tcacagtagc | 720 |
| tccagtacac atttgtacaa gctgggagtc cgcctcaggg atcgtggagt tctgggtaga | 780 |
| tgggaagccc agggtgagga agagtctgaa gaagggatac actgtggggg cagaagcaag | 840 |
| catcatcttg gggcaggagc aggattcctt cggtgggaac tttgaaggaa gccagtccct | 900 |
| ggtgggagac attggaaatg tgaacatgtg ggactttgtg ctgtcaccag atgagattaa | 960 |
| caccatctat cttggcgggc ccttcagtcc taatgtcctg aactggcggg cactgaagta | 1020 |
| tgaagtgcaa ggcgaagtgt tcaccaaacc ccagctgtgg ccctgaggcc cagctgtggg | 1080 |
| tcctgaaggt acctcccggt tttttacacc gcatgggccc cacgtctctg tctctggtac | 1140 |
| ctcccgcttt tttacactgc atggttccca cgtctctgtc tctgggcctt tgttcccta | 1200 |
| tatgcattgc aggcctgctc caccctcctc agcgcctgag aatggaggta aagtgtctgg | 1260 |
| tctgggagct cgttaactat gctgggaaac ggtccaaaag aatcagaatt tgaggtgttt | 1320 |
| tgttttcatt tttatttcaa gttggacaga tcttggagat aatttcttac ctcacataga | 1380 |
| tgagaaaact aacacccaga aaggagaaat gatgttataa aaaactcata aggcaagagc | 1440 |
| tgagaaggaa gcgctgatct tctatttaat tccccaccca tgaccccag aaagcaggag | 1500 |
| ggcattgccc acattcacag ggctcttcag tctcagaatc aggacactgg ccaggtgtct | 1560 |
| ggtttgggtc cagagtgctc atcatcatgt catagaactg ctgggcccag gtctcctgaa | 1620 |
| atgggaagcc cagcaatacc acgcagtccc tccactttct caaagcacac tggaaaggcc | 1680 |
| attagaattg ccccagcaga gcagatctgc ttttttttcca gagcaaaatg aagcactagg | 1740 |
| tataaatatg ttgttactgc caagaactta aatgactggt ttttgtttgc ttgcagtgct | 1800 |
| ttcttaattt tatggctctt ctgggaaact cctccccttt tccacacgaa ccttgtgggg | 1860 |
| ctgtgaattc tttcttcatc cccgcattcc caatatatccc aggccacaag agtggacgtg | 1920 |
| aaccacaggg tgtcctgtca gaggagccca tctcccatct ccccagctcc ctatctggag | 1980 |
| gatagttgga tagttacgtg ttcctagcag gaccaactac agtcttccca aggattgagt | 2040 |
| tatggacttt gggagtgaga catcttcttg ctgctggatt tccaagctga gggacgtga | 2100 |
| acctgggacc accagtagcc atcttgtttg ccacatggag agagactrtg aggacagaag | 2160 |
| ccaaactgga agtggaggag ccaagggatt gacaaacaac agagccttga ccacgtggag | 2220 |
| tctctgaatc agccttgtct ggaaccagat ctacacctgg actgcccagg tctataagcc | 2280 |
| aataaagccc ctgtttactt g | 2301 |

<210> SEQ ID NO 4
<211> LENGTH: 921
<212> TYPE: DNA
<213> ORGANISM: Homo sapiens
<220> FEATURE:
<221> NAME/KEY: variation
<222> LOCATION: (422)..(422)
<223> OTHER INFORMATION: Synthetic C or T

<400> SEQUENCE: 4

| | |
|---|---|
| ctttagtttt tgctcctcaa attggaataa tgatagaatg agagtactaa aaccccaca | 60 |
| actggcccta catgaatggc cagctatctc aaaagaggga ctgtgcttgt cagagggaat | 120 |
| cccttcaggg gactcttgga caggttaaag tgccatggat atgttgtgta atgggaagtg | 180 |

```
taaacttaca gggacttgat ttcaaaggtc attagagaag ttagccacaa cttctaaagc    240
aactatcaga aaacagcttg gactcactca agtaaacagg ggctttattg gcttatagac    300
ctgggcagtc caggtgtaga tctggttcca gacaaggctg attcagagac tccacgtggt    360
caaggctctg ttgtttgtca atcccttggc tcctccactt ccagtttggc ttctgtcctc    420
ayagtctctc tccatgtggc aaacaagatg gctactggtg gtcccaggtt cacgtcctct    480
cagcttggaa atccagcagc aagaagatgt ctcactccca aagtccataa ctcaatcctt    540
gggaagactg tagttggtcc tgctaggaac acgtaactat ccaactatcc tccagatagg    600
gagctgggga gatgggagat gggctcctct gacaggacac cctgtggttc acgtccactc    660
ttgtggcctg ggtatattgg gaatgcgggg atgaagaaag aattcacagc cccacaaggt    720
tcgtgtggaa aaggggagga gtttcccaga agagccataa aattaagaaa gcactgcaag    780
caaacaaaaa ccagtcattt aagttcttgg cagtaacaac atatttatac ctagtgcttc    840
attttgctct ggaaaaaaag cagatctgct ctgctggggc aattctaatg gcctttccag    900
tgtgctttga gaaagtggag g                                              921
```